United States Patent [19]

Barrett

[11] Patent Number: 5,204,091
[45] Date of Patent: Apr. 20, 1993

[54] METHOD FOR COMBATTING FOOT ODORS

[76] Inventor: Lawrence E. Barrett, 46198 First Avenue, Chilliwack, British Columbia, Canada, V2P 1W3

[21] Appl. No.: 803,425

[22] Filed: Dec. 6, 1991

[51] Int. Cl.$^5$ .......... A61K 7/32; A61K 33/26
[52] U.S. Cl. .......... 424/65; 424/608; 424/647
[58] Field of Search .......... 424/65

[56] References Cited

FOREIGN PATENT DOCUMENTS 63-315200 12/1988 Japan .......... 424/65
2-102655 4/1990 Japan .......... 424/65

OTHER PUBLICATIONS

The Merck Index, 1976, p. 523, #3936.

Primary Examiner—Dale R. Ore
Attorney, Agent, or Firm—John Russell Uren

[57] ABSTRACT

A method of combatting foot odors comprising the step of soaking the feet in a soaking solution comprising as active ingredient, ferric ferrocyanide, represented by the formula $Fe(III)_4[FE(CN)_6]_3$, in an aqueous oxalic acid solution.

10 Claims, No Drawings

METHOD FOR COMBATTING FOOT ODORS

FIELD OF THE INVENTION

This invention relates to a composition and method for combatting body odors such as a deodorant or odor suppressant composition which can be used as a foot soaking solution.

BACKGROUND OF THE INVENTION

Foot soaking solutions are known for the treatment of certain foot ailments or for the purpose of relaxing the feet. It is an object of the present invention to provide a deodorant composition which can be used as a foot soaking solution in a footbath and which is effective as an odor suppressant.

SUMMARY OF THE INVENTION

According to the invention, there is provided a deodorant composition comprising, as active ingredient, ferric ferrocyanide, represented by the formula $Fe(III)_4[FE(CN)_6]_3$, in an aqueous oxalic acid solution.

Also according to the invention, there is provided a foot soaking composition comprising, as active ingredient, ferric ferrocyanide, represented by the formula $Fe(III)_4[FE(CN)_6]_3$, in an aqueous oxalic acid solution.

Further according to the invention, there is provided a method of combatting foot odors comprising the step of soaking the feet in a soaking solution comprising, as active ingredient, ferric ferrocyanide in an aqueous oxalic acid solution.

Also according to the invention, there is provided a method of preparing a foot soaking solution comprising the step of dissolving ferric ferrocyanide, as active ingredient, in an aqueous oxalic acid solution.

The oxalic acid solution may contain from about 1 g to about 5 g and preferably about 1.25 g oxalic acid per 1 liter of water. The deodorant composition may comprise from about 5 g to about 50 g and preferably about 10 g of ferric ferrocyanide per 1 liter of the aqueous oxalic acid solution. According to another embodiment of the invention, the deodorant composition contains from about 8 g to about 50 g of ferric ferrocyanide per 1 liter of oxalic acid solution.

Further objects and advantages of the invention will become apparent from the description of a preferred embodiment of the invention below.

DETAILED DESCRIPTION

The invention will now be described by way of one specific example.

A foot soaking solution is prepared by dissolving 11 g of ferric ferrocyanide $Fe(III)_4[FE(CN)_6]_3$ in 1 liter of an aqueous oxalic acid solution. The oxalic acid solution is prepared by dissolving 1.25 g of oxalic acid per 1 liter of water. In a preferred embodiment, the ferric ferrocyanide and oxalic acid are provided as a dry mixture which can then simply be added to the water.

The deodorant may be used at room temperature or any other temperature which is comfortable for the user.

It is known that ferric ferrocyanide, also known as insoluble "Prussian Blue" or insoluble "Turnbull's Blue" is practically insoluble in water, dilute acids and most organic solvents but that it is soluble in a freshly prepared aqueous oxalic acid solution. Thus, the purpose of the oxalic acid in the present application is merely to bring the otherwise insoluble ferric ferrocyanide into solution so that it is in a form suitable for use as a footbath.

The chemistry of ferric ferrocyanide in solution is complex and the nature of the ions which are present in solution when the ferrocyanide is dissolved in oxalic acid is not fully understood, but it is believed that no free iron ions are present in the resulting solution. It has been established by tests performed on feet soaked in the solution that it is effective in combatting or suppressing foot odors.

While only a preferred embodiment of the invention have been described herein in detail, the invention is not limited thereby and modifications can be made within the scope of the attached claims.

What is claimed is:

1. A method of combatting foot odors comprising the step of soaking the feet in a soaking solution comprising, as active ingredient, ferric ferrocyanide in an aqueous oxalic acid solution.

2. A method of preparing a foot soaking solution comprising the step of dissolving ferric ferrocyanide, as active ingredient, in an aqueous oxalic acid solution.

3. A method of preparing a foot soaking solution according to claim 2, wherein the oxalic acid solution contains from about 1 g to about 5 g oxalic acid per 1 liter of water.

4. A method of preparing a foot soaking solution according to claim 3, wherein the oxalic acid solution contains about 1.25 g oxalic acid per 1 liter of water.

5. A method of preparing a foot soaking solution according to claim 2, comprising from about 5 g to about 50 g of ferric ferrocyanide per 1 liter of the aqueous oxalic acid solution.

6. A method of preparing a foot soaking solution according to claim 5, comprising dissolving about 10 g of ferric ferrocyanide per 1 liter of the aqueous oxalic acid solution.

7. The method according to claim 1, wherein the oxalic acid solution contains from about 1 g to about 5 g oxalic acid per 1 liter of water.

8. The method according to claim 7, wherein the oxalic acid solution contains about 1.25 g oxalic acid per 1 liter of water.

9. The method according to claim 1, wherein the solution comprises from about 5 g to about 50 g of ferric ferrocyanide per 1 liter of the aqueous oxalic acid solution.

10. The method according to claim 9, wherein the solution comprises about 10 g of ferric ferrocyanide per 1 liter of aqueous oxalic acid solution.

* * * * *